(12) United States Patent
Matsuzaki et al.

(10) Patent No.: US 9,782,194 B2
(45) Date of Patent: Oct. 10, 2017

(54) MEDICAL APPARATUS SYSTEM AND LIQUID SUPPLY DEVICE

(71) Applicant: SEIKO EPSON CORPORATION, Tokyo (JP)

(72) Inventors: Takahiro Matsuzaki, Shiojiri (JP); Kazuaki Uchida, Fujimi-machi (JP); Shinichi Miyazaki, Suwa (JP)

(73) Assignee: SEIKO EPSON CORPORATION, Tokyo (JP)

( * ) Notice: Subject to any disclaimer, the term of this patent is extended or adjusted under 35 U.S.C. 154(b) by 319 days.

(21) Appl. No.: 14/490,908

(22) Filed: Sep. 19, 2014

(65) Prior Publication Data

US 2015/0088176 A1    Mar. 26, 2015

(30) Foreign Application Priority Data

Sep. 20, 2013  (JP) .................................. 2013-194886

(51) Int. Cl.
*A61B 17/3203*    (2006.01)
*A61B 17/00*    (2006.01)

(52) U.S. Cl.
CPC ..................... *A61B 17/3203* (2013.01); *A61B 2017/00154* (2013.01)

(58) Field of Classification Search
CPC .................................................. A61B 17/3203
See application file for complete search history.

(56) References Cited

U.S. PATENT DOCUMENTS

| 5,135,482 A * | 8/1992 | Neracher ......... A61B 17/32037 604/22 |
| 5,836,909 A * | 11/1998 | Cosmescu .............. A61B 18/14 600/108 |
| 2002/0116021 A1* | 8/2002 | Gordon .............. A61B 17/3203 606/167 |
| 2007/0129680 A1 | 6/2007 | Hagg et al. |
| 2008/0289398 A1* | 11/2008 | Khashayar .......... A61F 9/00736 73/37 |
| 2009/0043480 A1* | 2/2009 | Seto .................... A61B 17/3203 701/103 |
| 2010/0069937 A1* | 3/2010 | Seto ................. A61B 17/32037 606/167 |

(Continued)

FOREIGN PATENT DOCUMENTS

| JP | 2001-292963 A | 10/2001 |
| JP | 2010-075589 A | 4/2010 |
| JP | 2010-084564 A | 4/2010 |

OTHER PUBLICATIONS

Extended European Search Report dated Dec. 23, 2014 as received in Application No. 14185317.6.

*Primary Examiner* — Shaun L David
(74) *Attorney, Agent, or Firm* — Maschoff Brennan

(57) ABSTRACT

A medical apparatus system includes: a medical apparatus having an ejection unit which ejects a liquid; and a liquid supply device which supplies the liquid to the medical apparatus. The liquid supply device includes: a supply channel through which the liquid is supplied to the ejection unit; a pressurizing unit which pressurizes the liquid in the supply channel; a blocking unit which blocks the supply channel; and a control unit which causes the pressurizing unit to pressurize the liquid in the supply channel in the state where the supply channel is blocked by the blocking unit.

4 Claims, 9 Drawing Sheets

(56) References Cited

U.S. PATENT DOCUMENTS

| | | | |
|---|---|---|---|
| 2010/0078495 A1* | 4/2010 | Seto | A61B 17/3203 239/1 |
| 2010/0079522 A1* | 4/2010 | Seto | B41J 2/175 347/14 |
| 2010/0082053 A1* | 4/2010 | Hama | A61B 17/3203 606/167 |
| 2010/0082054 A1* | 4/2010 | Seto | A61B 17/3203 606/167 |
| 2010/0111708 A1* | 5/2010 | Seto | A61B 17/3203 417/44.1 |
| 2011/0036859 A1* | 2/2011 | Matsuzaki | A61B 17/3203 604/131 |
| 2011/0037795 A1* | 2/2011 | Kojima | A61B 17/3203 347/10 |
| 2011/0190804 A1* | 8/2011 | Sekino | A61B 17/3203 606/190 |
| 2011/0208224 A1* | 8/2011 | Kojima | F04B 43/04 606/167 |
| 2011/0238098 A1* | 9/2011 | Sekino | A61B 17/3203 606/167 |
| 2012/0046605 A1* | 2/2012 | Uchida | A61B 17/3203 604/65 |
| 2012/0046681 A1* | 2/2012 | Kojima | A61B 17/3203 606/167 |
| 2012/0181352 A1* | 7/2012 | Seto | A61B 17/3203 239/101 |
| 2013/0138082 A1 | 5/2013 | Salahieh et al. | |
| 2013/0144207 A1* | 6/2013 | Gonon | A61B 17/3203 604/70 |
| 2013/0310862 A1* | 11/2013 | Seto | A61B 17/3203 606/167 |
| 2014/0142536 A1* | 5/2014 | Hagg | A61M 5/30 604/500 |
| 2014/0296895 A1* | 10/2014 | Kojima | A61B 17/3203 606/167 |

\* cited by examiner

| FLOW RATE Q (ml / min) | SUPPLY PRESSURE SP (kPa) |
|---|---|
| 3 ≤ Q < 4 | 20 |
| 4 ≤ Q < 5 | 30 |
| 5 ≤ Q < 6 | 40 |
| 6 ≤ Q < 7 | 50 |
| ⋮ | ⋮ |
| 10 ≤ Q < 12 | 80 |
| ⋮ | ⋮ |

| APPLIED VOLTAGE E (V) | SUPPLY PRESSURE SP (kPa) |
|---|---|
| 0 ≤ E < 5 | 50 |
| 5 ≤ E < 10 | 60 |
| 10 ≤ E < 15 | 70 |
| 15 ≤ E < 20 | 75 |
| ⋮ | ⋮ |
| 35 ≤ E < 40 | 90 |
| ⋮ | ⋮ |

MEDICAL APPARATUS SYSTEM AND LIQUID SUPPLY DEVICE

This patent application claims the benefit of Japanese Patent Application No. 2013-194886, filed on Sep. 20, 2013. The content of the aforementioned application is hereby incorporated by reference in its entirety.

BACKGROUND

1. Technical Field

The present invention relates to a technique for supplying a liquid to a medical apparatus.

2. Related Art

The technique of JP-A-2001-292963 is known as a technique for improving responsiveness of liquid ejection and stop in a medical apparatus which ejects a liquid. JP-A-2001-292963 discloses a technique in which cleaning water is pressure-fed by a pump to a cleaning water feeding channel of an endoscope via a water feeding tube and in which the pump is operated reversely for a predetermined time immediately after the operation of the pump is stopped, thus lowering the pressure of the pressure-fed cleaning water in the water feeding tube.

However, the technique of JP-A-2001-292963 improves responsiveness of the stop of water feeding but cannot improve responsiveness of the start of water feeding.

SUMMARY

An advantage of some aspects of the invention is to solve at least a part of the problems described above, and the invention can be implemented as the following forms.

(1) An aspect of the invention provides a medical apparatus system. The medical apparatus system includes: a medical apparatus having an ejection unit which ejects a liquid; and a liquid supply device which supplies the liquid to the medical apparatus. The liquid supply device includes: a supply channel through which the liquid is supplied to the ejection unit; a pressurizing unit which pressurizes the liquid in the supply channel; a blocking unit which blocks the supply channel; and a control unit which causes the pressurizing unit to pressurize the liquid in the supply channel in the state where the supply channel is blocked by the blocking unit. According to the medical apparatus system of this configuration, the liquid in the supply channel is pressurized in the state where the supply channel is blocked by the blocking unit. Therefore, when the blocking unit releases the channel, the liquid that is pressurized in advance can be supplied stably to the medical apparatus.

(2) In the medical apparatus system according to the aspect of the invention described above, the control unit may cause the blocking unit to block the supply channel when the ejection unit stops the ejection. According to the medical apparatus system of this configuration, responsiveness of the stop of ejection can be improved when the ejection unit of the medical apparatus stops the ejection.

(3) In the medical apparatus system according to the aspect of the invention described above, the medical apparatus system may further include a pressure setting unit which sets a first pressure that is a pressure with which the pressurizing unit pressurizes the liquid when the ejection unit ejects the liquid, and the control unit may set a second pressure that is a pressure with which the pressurizing unit pressurizes the liquid in the supply channel in the state where the supply channel is blocked by the blocking unit, on the basis of the first pressure that is set. According to the medical apparatus system of this configuration, the liquid pressurized with a proper pressure corresponding to the first pressure that is set can be supplied to the medical apparatus.

(4) In the medical apparatus system according to the aspect of the invention described above, the ejection unit may include an actuator which provides a pulsed flow for the ejected liquid, and an applied voltage setting unit which sets an applied voltage for driving the actuator, and the control unit may set a second pressure that is a pressure with which the pressurizing unit pressurizes the liquid in the supply channel in the state where the supply channel is blocked by the blocking unit, on the basis of the applied voltage that is set. According to the medical apparatus system of this configuration, the liquid pressurized with a proper pressure corresponding to the applied voltage for driving the actuator can be supplied to the medical apparatus.

(5) Another aspect of the invention provides a liquid supply device which supplies a liquid to a medical apparatus. The liquid supply device includes: a supply channel through which the liquid is supplied to the medical apparatus; a pressurizing unit which pressurizes the liquid in the supply channel; a blocking unit which blocks the supply channel; and a control unit which causes the pressurizing unit to pressurize the liquid in the supply channel in the state where the supply channel is blocked by the blocking unit. According to the liquid supply device of this configuration, the liquid in the supply channel is pressurized in the state where the supply channel is blocked by the blocking unit. Therefore, when the blocking unit releases the channel, the liquid that is pressurized in advance can be supplied stably to the medical apparatus.

Not all the plural components of each of the above configurations are essential. In order to solve a part or the whole of the foregoing problem or in order to achieve a part or the whole of the advantages described herein, a part of the plural components can be changed, deleted, replaced with another component, or partly deleted in a limited context. Also, in order to solve a part or the whole of the foregoing problem or in order to achieve a part or the whole of the advantages described herein, a part or the whole of the technique features included in one of the above configurations can be combined with a part or the whole of the technical features included in another one of the above configurations, thus forming a separate configuration of the invention.

For example, as a configuration of the invention, a system including one or more of two components of a medical apparatus and a liquid supply device can be realized. Also, the liquid supply device can be realized as a device including one or more of four components of a supply channel, a pressurizing unit, a blocking unit, and a control unit. That is, the system may or may not include the medical apparatus. The system may or may not include the liquid supply device. The liquid supply device may or may not include the supply channel. The liquid supply device may or may not include the pressurizing unit. The liquid supply device may or may not include the blocking unit. The liquid supply device may or may not include the control unit. The medical apparatus may be configured as a medical apparatus having an ejection unit which ejects a liquid. The liquid supply device may be configured as a liquid supply device which supplies the liquid to the medical apparatus. The supply channel may be configured as a supply channel through which the liquid is supplied to the ejection unit. The pressurizing unit may be configured as a pressurizing unit which pressurizes the liquid in the supply channel. The blocking unit may be configured as a blocking unit which blocks the supply channel. The control unit may be configured as a control unit which causes the pressurizing unit to pressurize the liquid in the supply channel in the state where the supply channel is blocked by the blocking unit. Such a system can be realized, for example, as a medical apparatus system but can also be realized as other system than a medical apparatus system. According to such a configuration, at least one of various problems such as miniaturization of the structure, lower cost, saving of resources, easier manufacturing, and improved user-friendliness can be solved. A part or the whole of the technique features of each configuration of the medical apparatus system can be applied to this system.

The invention can also be implemented in various other forms other than a system. For example, the invention can be implemented in the form of a liquid supply method, a liquid ejection device, a liquid ejection method, a medical apparatus or the like.

BRIEF DESCRIPTION OF THE DRAWINGS

The invention will be described with reference to the accompanying drawings, wherein like numbers reference like elements.

FIG. 9 is an explanatory view showing a medical apparatus system 10a.

DESCRIPTION OF EXEMPLARY EMBODIMENTS

A. First Embodiment

A1. Configuration of Medical Apparatus System

Figure 1:
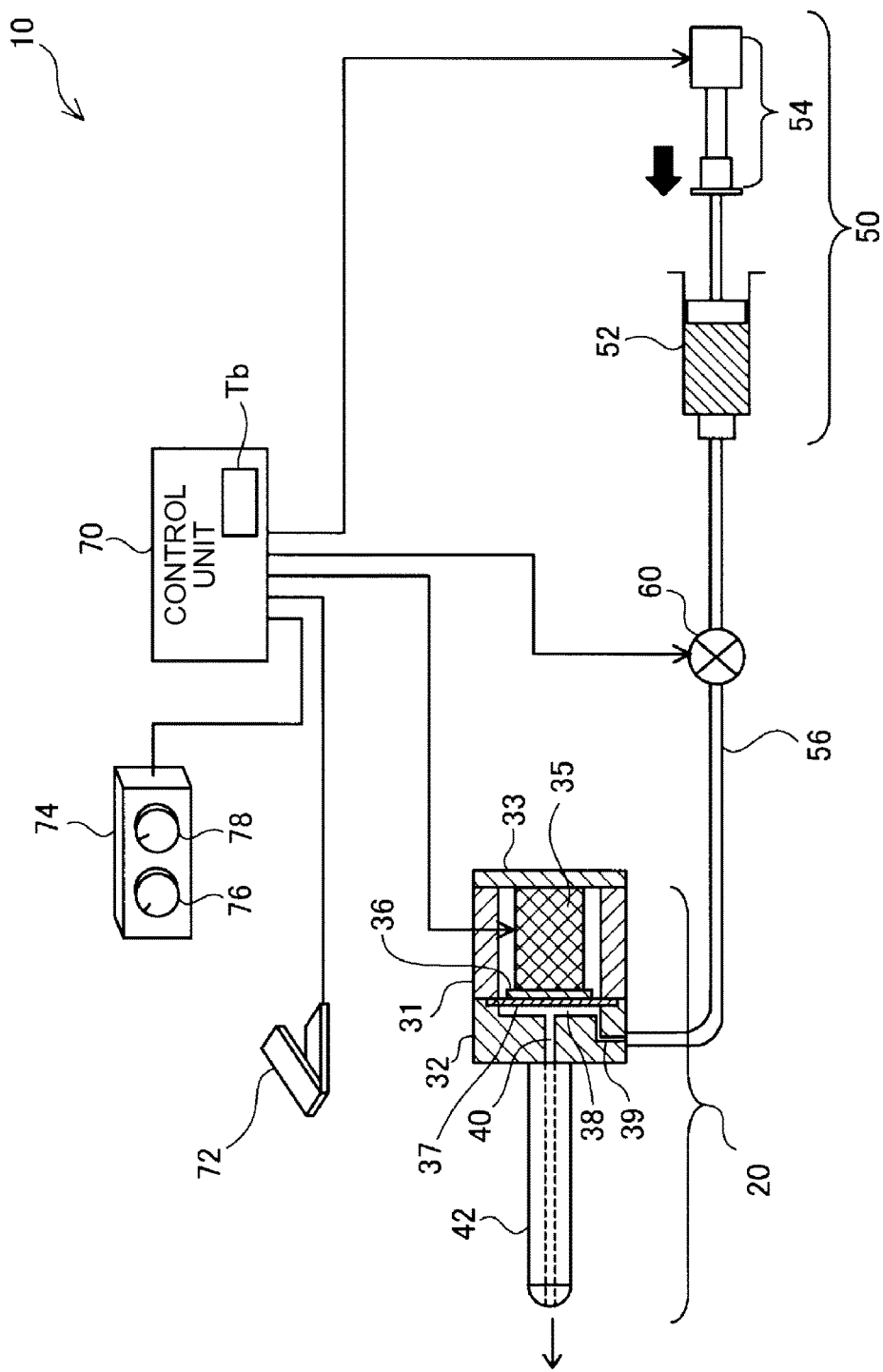
FIG. 1 is an explanatory view showing the configuration of a medical apparatus system 10.

FIG. 1 is an explanatory view illustrating the configuration of a medical apparatus system 10 as a first embodiment of the invention. The medical apparatus system 10 is used as a surgical knife which ejects a liquid to an affected part and thus incises or excises the affected part.

The medical apparatus system 10 includes a liquid ejection device 20 as a medical apparatus, a liquid supply unit 50, and a control unit 70. The liquid ejection device 20 and the liquid supply unit 50 are connected to each other via a liquid supply channel 56. In this embodiment, the liquid supply channel 56 is made of polyvinyl chloride. The liquid supply channel 56 may also be made of various resins such as silicone or thermoplastic elastomer. A blocking unit 60 is installed on the liquid supply channel 56. A foot switch 72 and an ejection condition setting unit 74 are connected to the control unit 70. The control unit 70 also stores table data Tb.

The liquid supply unit 50 supplies a liquid to the liquid ejection device 20. The liquid supply unit 50 has a syringe 52 and a pressurizing unit 54. The syringe 52 accommodates a physiological saline solution as the liquid. As the liquid, various other liquids such as sterilized water for medical use and pure water can also be employed. The pressurizing unit 54 is an actuator which presses the syringe 52 and thus pressurizes the liquid inside the syringe 52. In this embodiment, the pressurizing unit 54 has a linear motor. As the linear motor is horizontally driven, the syringe 52 is pressed and the liquid inside the syringe 52 is pressurized. The liquid inside the syringe 52 pressurized by the pressurizing unit 54 is supplied to the liquid ejection device 20 via the liquid supply channel 56.

The liquid ejection device 20 provides pulsation for the liquid supplied from the liquid supply unit 50 and ejects the pulsed liquid. The user of the medical apparatus system 10 applies the pulsed liquid ejected from the liquid ejection device 20 to an affected part of a patient and thus incises or excises the affected part.

The liquid ejection device 20 includes a first case 31, a second case 32, a third case 33, a piezoelectric element 35, a reinforcement board 36, a diaphragm 37, and an ejection tube 42. The first case 31 is a cylindrical member. One end of the first case 31 is joined to the second case 32. The other end of the first case 31 is sealed by the third case 33. The piezoelectric element 35 is arranged in the space formed inside the first case 31.

The piezoelectric element 35 is a multilayer piezoelectric element. One end of the piezoelectric element 35 is fixed to the diaphragm 37 via the reinforcement board 36. The other end of the piezoelectric element 35 is fixed to the third case 33. The diaphragm 37 is made of a metallic thin film and the peripheral edge thereof is fixed to the first case 31. A housing chamber 38 is formed between the diaphragm 37 and the second case 32. The housing chamber 38 is changed in volume by the driving of the piezoelectric element 35.

A first channel 39 which causes the liquid to flow into the housing chamber 38 is formed in the second case 32. The first channel 39 is connected to the liquid supply channel 56. Also, a second channel 40 which causes the liquid housed in the housing chamber 38 to flow out is formed in the second case 32. The second channel 40 is connected to the ejection tube 42. The operation of the liquid ejection device 20 thus configured is controlled by the control unit 70.

The control unit 70 controls the operation of the entire medical apparatus system 10. The foot switch 72, which the user operates with a foot, is connected to the control unit 70. As the user turns on the foot switch 72, the control unit 70 controls the liquid supply unit 50 to supply the liquid to the liquid ejection device 20 (housing chamber 38) and also transmits a drive signal to the piezoelectric element 35. The liquid supplied from the liquid supply unit 50 flows into the housing chamber 38 via the liquid supply channel 56 and the first channel 39.

As the piezoelectric element 35 receives the drive signal from the control unit 70, the piezoelectric element 35 oscillates at a predetermined frequency. As the piezoelectric element 35 oscillates, the volume of the housing chamber 38 changes via the diaphragm 37 and the liquid housed in the housing chamber 38 is pressurized. Pulsation is provided for the liquid pressurized or depressurized at the predetermined frequency. The liquid is ejected outside as a pulsed liquid through the second channel 40 and the ejection tube 42.

The pulsed liquid refers to a liquid in the state where the flow rate or flow speed varies. The way to eject the liquid in a pulsed form may include intermittent ejection in which ejection and stop are repeated. However, since it suffices that the flow rate or flow speed of the liquid varies, the ejection of the pulsed liquid need not necessarily be intermittent ejection.

The ejection condition setting unit 74 for the user to set an ejection condition of the liquid is connected to the control unit 70. The ejection condition setting unit 74 includes a flow rate setting unit 76 and an applied voltage setting unit 78.

The flow rate setting unit 76 is a dial-type operation unit for the user to set a flow rate Q (ml/min) of the liquid supplied from the liquid supply unit 50 to the liquid ejection device 20. The applied voltage setting unit 78 is a dial-type operation unit for the user to set an applied voltage E (V) of the drive signal transmitted to the piezoelectric element 35.

The user can adjust the combination of the value of the flow rate Q and the value of the applied voltage E and thus set various ejection conditions of the liquid ejected from the liquid ejection device 20, such as the ejection pressure, flow rate, and droplet shape of the liquid ejected from the liquid ejection device 20. The ejection condition setting unit 74 may also include other operation units than the flow rate setting unit 76 and the applied voltage setting unit 78. The ejection condition setting unit 74 may include operation units for setting various other ejection conditions, for example, a frequency setting unit for the user to set a frequency of the applied voltage E, and a waveform setting unit for the user to set a waveform of the drive signal, or the like.

The control unit 70 stores the table data Tb. The table data Tb is a two-dimensional lookup table which outputs a pressure (supply pressure SP) with which the liquid supply unit 50 supplies the liquid, with respect to the two parameters of the flow rate Q and the applied voltage E. The table data Tb will be described in detail later.

Figure 2:
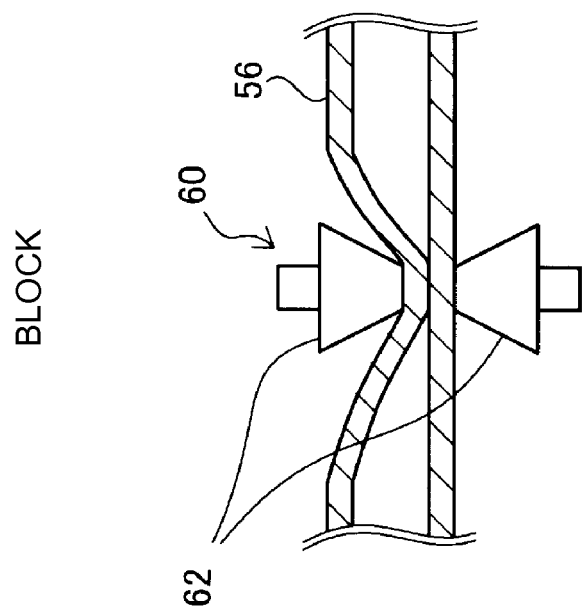
FIG. 2 is an explanatory view showing a blocking unit.
Figure 2:
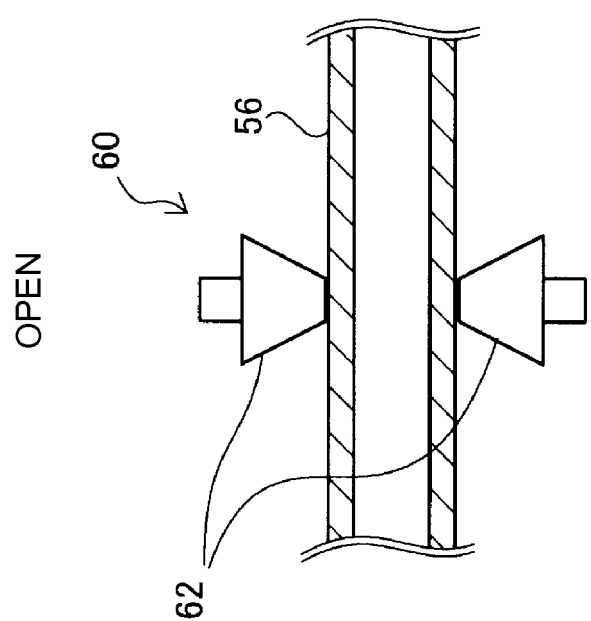

The blocking unit 60 is provided on the liquid supply channel 56. The blocking unit 60 blocks and opens the liquid supply channel 56. FIG. 2 is an explanatory view illustrating the blocking unit 60. As illustrated, the blocking unit 60 has pressing parts 62. The pressing parts 62 of the blocking unit 60 sandwich and press the liquid supply channel 56 from outside, thus blocking the liquid supply channel 56. In this embodiment, the blocking unit 60 is a solenoid valve. As the blocking unit 60, various other valves capable of blocking the liquid supply unit 50 can be employed, such as a globe valve, ball valve, butterfly valve, or diaphragm valve. The operation of the blocking unit 60 is controlled by the control unit 70.

A2. Ejection Control Processing

Figure 3:
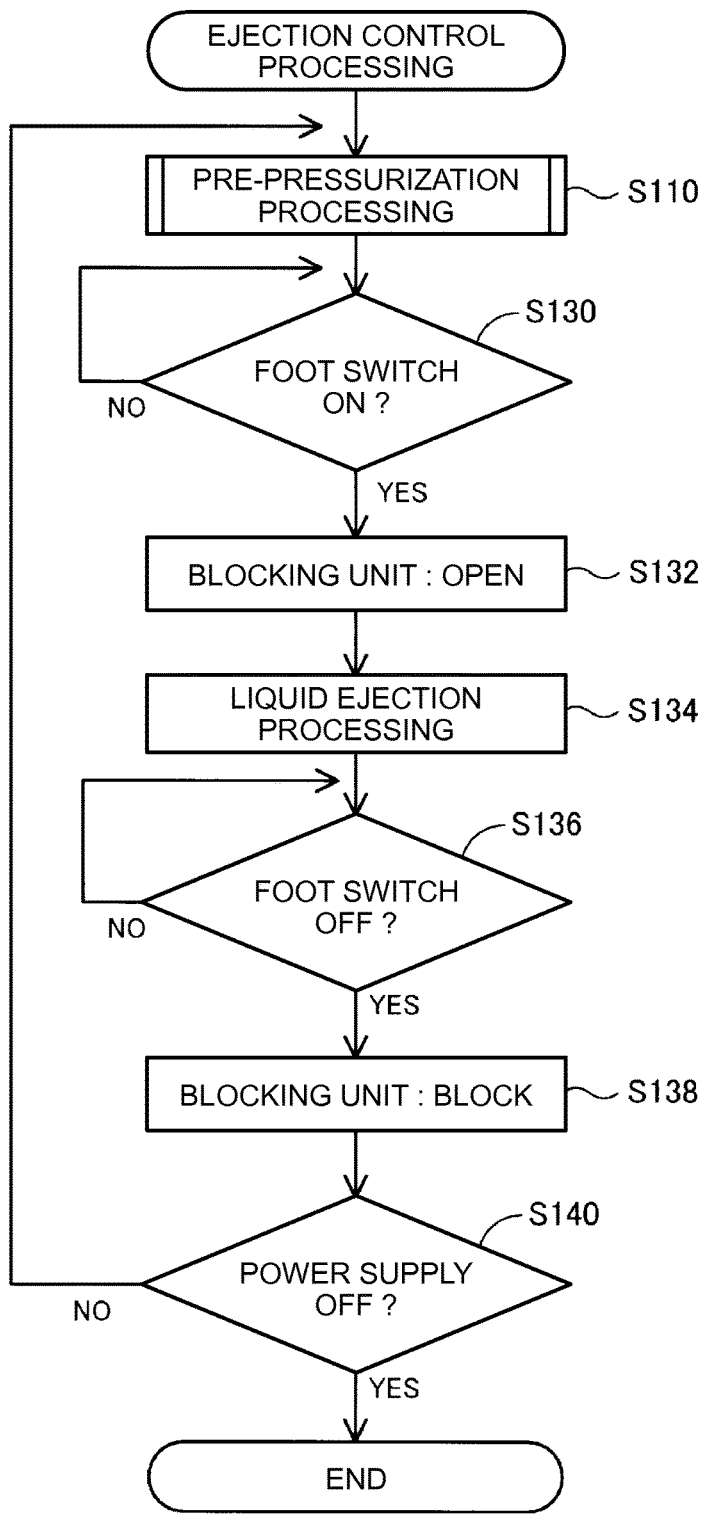
FIG. 3 is a flowchart showing the flow of ejection control processing.

Next, ejection control processing to control the ejection and stop of the liquid from the liquid ejection device 20 will be described. FIG. 3 is a flowchart showing the flow of the ejection control processing. The ejection control processing is started as the user turns on the power supply (not shown) of the medical apparatus system 10.

As the ejection control processing is started, the control unit 70 carries out pre-pressurization processing (Step S110), after the liquid supply unit 50 supplies the liquid to the liquid supply channel 56 and the liquid is supplied to the point in the liquid supply channel 56 to be blocked by the blocking unit 60. The pre-pressurization processing is processing to adjust the internal pressure of the liquid supply channel 56 in advance, in the state where the liquid supply channel 56 is blocked by the blocking unit 60 before the user turns on the foot switch 72. The pre-pressurization processing will be described in detail later.

As the user turns on the foot switch 72 (Step S130: YES), the control unit 70 controls the blocking unit 60 to open the liquid supply channel 56 (Step S132). Then, the control unit 70 carries out liquid ejection processing in which the liquid is ejected from the liquid ejection device 20 (Step S134). Specifically, the control unit 70 controls the liquid supply unit 50 to supply the liquid to the liquid ejection device 20 (housing chamber 38) and also transmits a drive signal to the piezoelectric element 35. As the liquid ejection processing is executed, the pulsed liquid is ejected from the liquid ejection device 20. The supply pressure SP, which is the pressure with which the liquid supply unit 50 supplies the liquid to the liquid ejection device 20, is determined by the control unit 70, using the flow rate Q, the applied voltage E, and the table data Tb, described below. The liquid supply unit 50 drives the pressurizing unit 54 under the control of the control unit 70 and supplies the liquid to the liquid ejection device 20 with the supply pressure SP.

As the user turns off the foot switch 72 (Step S136: YES), the control unit 70 controls the blocking unit 60 to block the liquid supply channel 56 (Step S138). The control unit 70 repeats the processing of Steps S110 to S138 until the user turns off the power supply of the medical apparatus system 10 (Step S140).

Figures 4A, 4B, 4C:
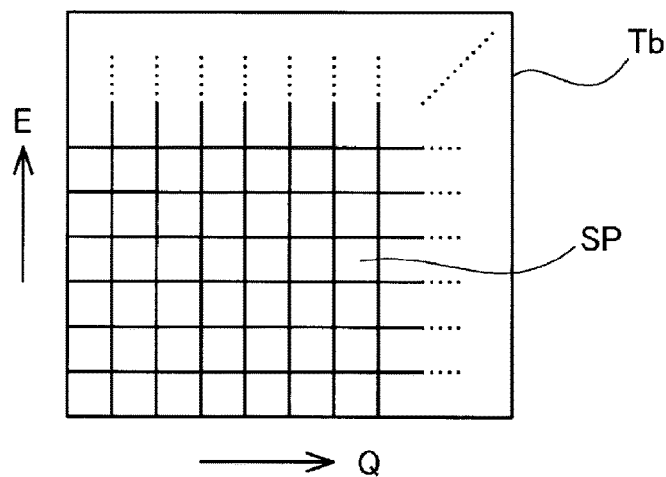
FIGS. 4A to 4C are explanatory views showing table data Tb.

Next, the table data Tb will be described. FIGS. 4A to 4C are explanatory views illustrating the table data Tb. First, the supply pressure SP (kPa) that is necessary for the liquid supply unit 50 to supply the liquid to the liquid ejection device 20 at the flow rate Q (ml/min) will be described. FIG. 4A is an explanatory view illustrating the relation between the flow rate Q and the supply pressure SP. For example, if the flow rate Q set by the user is $3 \leq Q < 4$, the liquid supply unit 50 needs to supply the liquid to the liquid ejection device 20 with the supply pressure SP of about 20 kPa. If the flow rate Q is $4 \leq Q < 5$, the liquid supply unit 50 needs to supply the liquid to the liquid ejection device 20 with the supply pressure SP of about 30 kPa. That is, the supply pressure SP needs to be changed according to the magnitude of the flow rate Q. In this embodiment, the relation between the flow rate Q and the supply pressure SP is acquired by actual measurement using the medical apparatus system 10. The relation between the flow rate Q and the supply pressure SP may also be acquired by a simulation.

Next, the applied voltage E (V) and the supply pressure SP (kPa) that is necessary for supplying the liquid to the liquid ejection device 20 will be described. FIG. 4B is an explanatory view illustrating the relation between the applied voltage E and the supply pressure SP. As shown in FIG. 4B, for example, if the applied voltage E is $0 \leq E < 5$ while the flow rate Q is a predetermined constant value, the liquid supply unit 50 needs to supply the liquid to the liquid ejection device 20 with the supply pressure SP of about 50 kPa. If the applied voltage E is $5 \leq E < 10$, the liquid supply unit 50 needs to supply the liquid to the liquid ejection device 20 with the supply pressure SP of about 60 kPa. In this embodiment, the relation between the applied voltage E and the supply pressure SP is acquired by actual measurement using the medical apparatus system 10. The relation between the applied voltage E and the supply pressure SP may also be acquired by a simulation.

Figure 5:
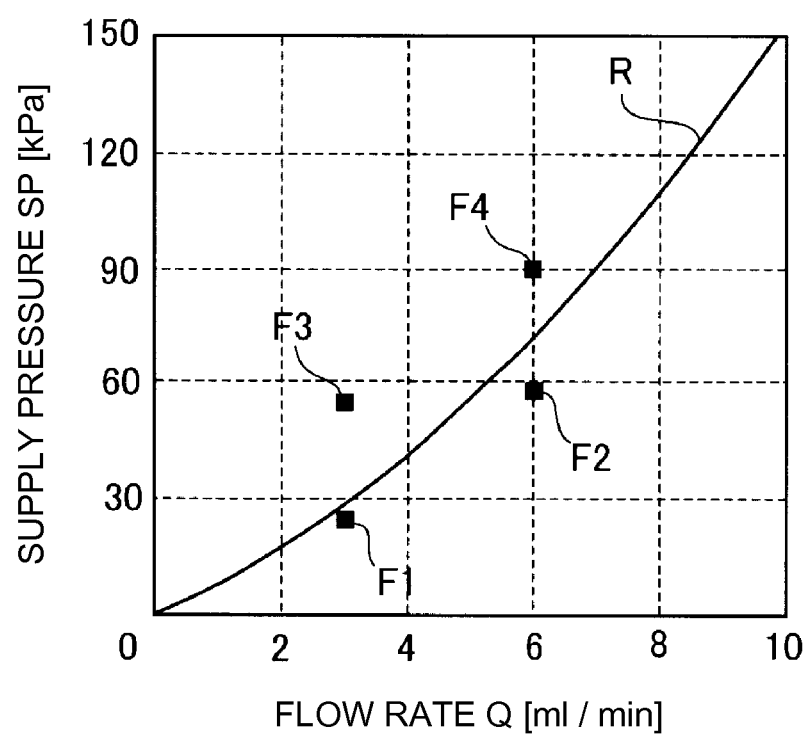
FIG. 5 shows the result of an experiment showing the relation between applied voltage E and supply pressure SP.

FIG. 5 shows the result of an experiment showing the relation between the applied voltage E, the supply pressure SP and the flow rate Q. Plotted points F1 and F2 shown in the graph of FIG. 5 show experimental values of the supply pressure SP for the liquid supply unit 50 to supply the liquid at each flow rate Q when no voltage is applied to the piezoelectric element 35. A curve R shows a theoretical value of the supply pressure SP for supplying the liquid at each flow rate Q when no voltage is applied to the piezoelectric element 35. Plotted points F3 and F4 show values of the supply pressure SP for the liquid supply unit 50 to supply the liquid at each flow rate Q when the applied voltage E is 60 (V).

As can be seen from FIG. 5, when the liquid is supplied at a constant flow rate Q from the liquid supply unit 50 to the liquid ejection device 20, the supply pressure SP needs to be changed according to the value of the applied voltage E. As the piezoelectric element 35 pressurizes the liquid, the liquid inside the first channel 39 is pressurized (see FIG. 1). At this point, a force in the opposite direction to the inflow direction acts on the liquid flowing into the first channel 39 from the liquid supply channel 56, due to the pressurization of the liquid by the piezoelectric element 35. Therefore, when the applied voltage E to drive the piezoelectric element 35 is increased, the supply pressure SP needs to be increased in order to supply the liquid to the liquid ejection device 20 at a constant flow rate Q.

FIG. 4C is an explanatory view illustrating the table data Tb. As described with reference to FIGS. 4A and 4B, the supply pressure SP needs to be set according to the preset values of the flow rate Q and the applied voltage E. In this embodiment, the proper supply pressure SP corresponding to the two parameters of the flow rate Q and the applied voltage E is recorded in the table data Tb. In this embodiment, the value of the supply pressure SP stored in the table data Tb is acquired by actual measurement using the medical apparatus system 10. The value of the supply pressure SP stored in the table data Tb may also be acquired by a simulation.

When carrying out the ejection control processing, the control unit 70 inputs the flow rate Q and the applied voltage E that are set via the ejection condition setting unit 74, into the table data Tb, and thus acquires the supply pressure SP. The control unit 70 controls the liquid supply unit 50 to pressurize the liquid with the supply pressure SP acquired from the table data Tb and to supply the liquid to the liquid ejection device 20.

A3. Pre-Pressurization Processing

Figure 6:
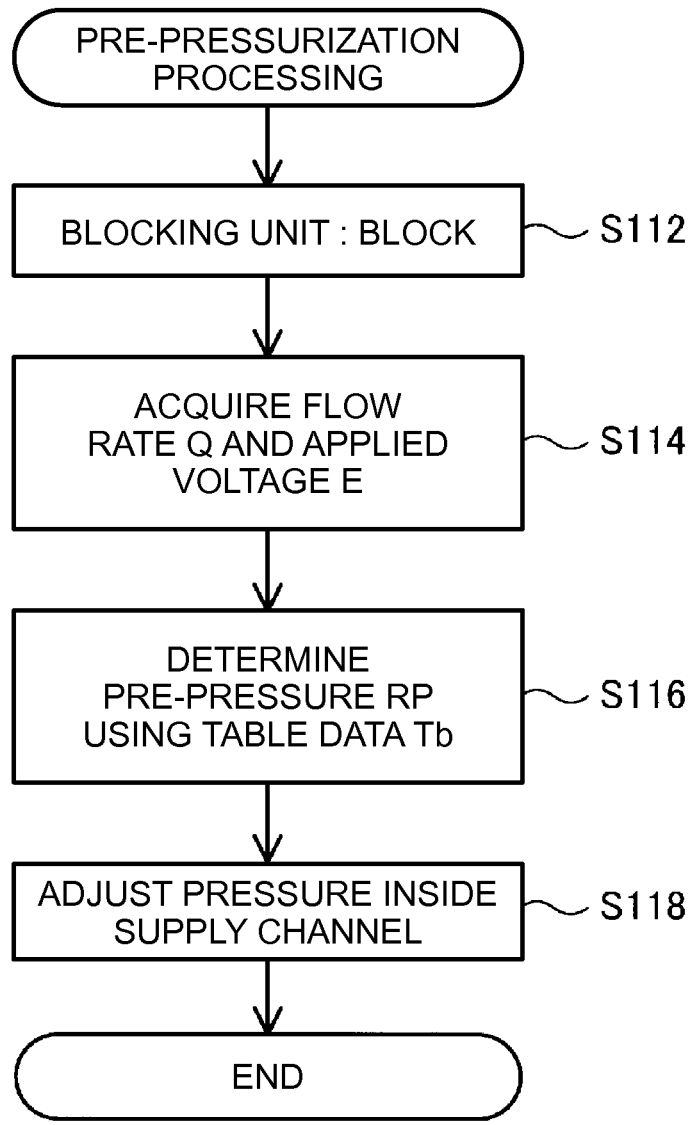
FIG. 6 is a flowchart showing the flow of pre-pressurization processing.

The pre-pressurization processing (Step S110 in FIG. 3) will now be described. FIG. 6 is a flowchart showing the flow of the pre-pressurization processing. As the pre-pressurization processing is started, the control unit 70 controls the blocking unit 60 to block the liquid supply channel 56 (Step S112). The control unit 70 then acquires the flow rate Q and the applied voltage E that are preset by the user via the ejection condition setting unit 74 (Step S114).

Subsequently, the control unit 70 determines a pre-pressure RP based on the flow rate Q and the applied voltage E (Step S116). The pre-pressure RP is the internal pressure of the liquid supply channel 56 in the state where the liquid supply channel 56 is blocked by the blocking unit 60. The control unit 70 inputs the flow rate Q and the applied voltage E set by the user into the table data Tb and determines the supply pressure SP outputted from the table data Tb as the pre-pressure RP. That is, in this embodiment, the supply pressure SP and the pre-pressure RP are the same value. While the pre-pressure RP is acquired using the table data Tb in this embodiment, separate table data for acquiring the pre-pressure RP may also be used. Also, the table data Tb may use table data for acquiring the pre-pressure RP corresponding to each type or device of the liquid ejection device 20, such as the device for incision operation or for endoscope, or corresponding to each type or channel of the liquid supply channel 56, such as the length or diameter of the channel.

After the pre-pressure RP is determined, the internal pressure of the liquid supply channel 56 is adjusted to the pre-pressure RP (Step S118). Specifically, the control unit 70 drives the pressurizing unit 54 to pressurize the liquid inside the syringe 52, thus adjusting the internal pressure of the liquid supply channel 56 to the pre-pressure RP. In this description, the pressurizing is not limited to increasing the internal pressure of the liquid supply channel 56 but also includes decreasing the internal pressure of the liquid supply channel 56. The control unit 70 carries out the pre-pressurization processing in this manner.

A4. Effects of Pre-Pressurization Processing

Figure 7:
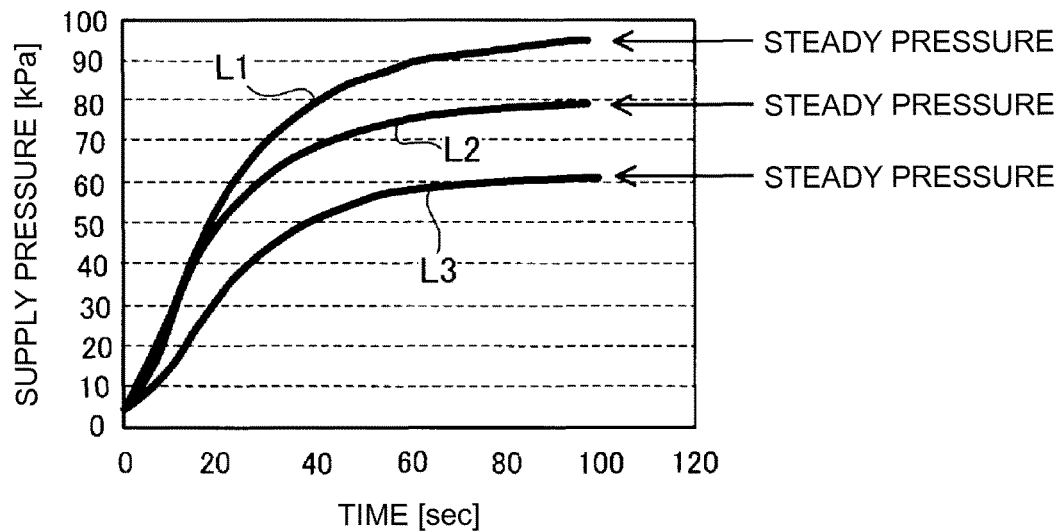
FIG. 7 is a graph showing characteristics of supply pressure.

The effects of the pre-pressurization processing will be described. First, a comparative example is shown in FIG. 7. FIG. 7 is a graph showing characteristics of the supply pressure in the case where the liquid supply unit 50 starts supplying the liquid to the liquid ejection device 20 without carrying out the pre-pressurization processing. The blocking unit 60 is constantly in the open state.

A line L1 shows the supply pressure characteristic in the case where the flow rate Q is set to 6 (ml/min). A line L2 shows the supply pressure characteristic in the case where the flow rate Q is set to 5 (ml/min). A line L3 shows the supply pressure characteristic in the case where the flow rate Q is set to 4 (ml/min). The applied voltage E is set to a predetermined value.

As can be seen from the lines L1 to L3, it takes 60 to 100 seconds for the supply pressure to reach s steady pressure after the liquid supply unit 50 starts supplying the liquid. The steady pressure means the supply pressure with which the liquid is normally supplied at each flow rate Q that is set. As illustrated, it takes 60 to 100 seconds until the liquid is supplied from the liquid supply unit 50 to the liquid ejection device 20 at a desired flow rate Q after the user turns on the foot switch 72. The fact that it takes a predetermined time for the supply pressure to reach the steady pressure is considered to be due to various factors such as the channel resistance of the liquid supply channel 56 and the channel deformation (channel expansion) of the liquid supply channel 56 due to elasticity.

In this embodiment, as the pre-pressurization control is carried out to adjust the internal pressure of the liquid supply channel 56 to the pre-pressure RP in advance, the time taken for the supply pressure to reach the steady pressure can be reduced when the liquid supply unit 50 starts supplying the liquid to the liquid ejection device 20.

A5. Effects

As described above, in the medical apparatus system 10, since the pre-pressurization processing is carried out, the pre-pressurized liquid can be supplied when the liquid supply unit 50 supplies the liquid to the liquid ejection device 20. Therefore, the time taken for the supply pressure of the liquid supplied from the liquid supply unit 50 to the liquid ejection device 20 to reach the steady pressure can be reduced. Thus, liquid ejection responsiveness at the time of starting the ejection of the liquid can be improved.

The medical apparatus system 10 has the table data Tb storing the proper value of the supply pressure SP corresponding to the flow rate Q and the applied voltage E. The control unit 70 acquires the pre-pressure RP based on the ejection conditions (flow rate Q and applied voltage E) set by the user and the table data Tb and carries out the pre-pressurization processing. Therefore, in the medical apparatus system 10, the pre-pressurization processing can be carried out with the proper pressure corresponding to the ejection conditions set by the user.

Figure 8:
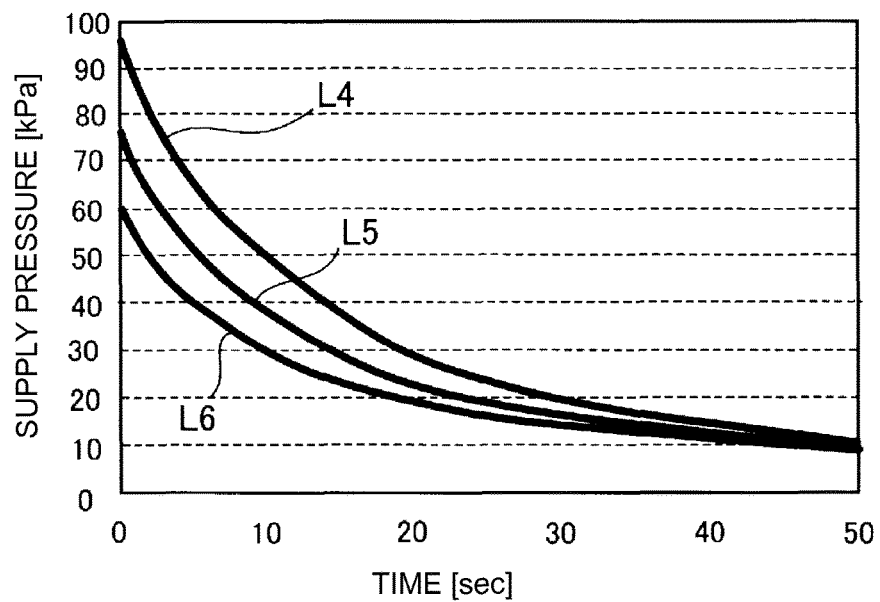
FIG. 8 is a graph showing attenuation characteristics of supply pressure.

The control unit 70 causes the blocking unit 60 to block the channel when stopping the ejection of the liquid from the liquid ejection device 20. Therefore, responsiveness of the stop of the liquid ejection can be improved. A comparative example is shown in FIG. 8. FIG. 8 is an explanatory view showing attenuation characteristics of the supply pressure in the liquid supply channel 56 in the case where the supply of the liquid from the liquid supply unit 50 is stopped without blocking the channel by the blocking unit 60. A line L4 shows the attenuation characteristic of the supply pressure in the liquid supply channel 56 in the case where the supply from the liquid supply unit 50, previously supplying the liquid at the flow rate Q of 6 (ml/min), is stopped. Lines L5 and L6 show the attenuation characteristic of the supply pressure in the liquid supply channel 56 in the case where the flow rate Q is 5 (ml/min) and 4 (ml/min), respectively. As can be seen from FIG. 8, the supply pressure gently attenuates after the liquid supply unit 50 stops the supply of the liquid. Therefore, when the blocking unit 60 does not block the liquid supply channel 56 with the stop of the ejection, the liquid is ejected from the liquid ejection device 20 for a predetermined period even if the user turns off the foot switch 72. Meanwhile, in the medical apparatus system 10 of this embodiment, when the user turns off the foot switch 72, the blocking unit 60 blocks the channel and therefore responsiveness of the stop of the ejection from the liquid ejection device 20, to the ejection stop operation by the user, can be improved.

B. Modifications

The invention is not limited to the above embodiment and can be carried out in various other forms without departing from the spirit and scope of the invention. For example, the following modifications can be made.

B1. Modification 1

Figure 9:
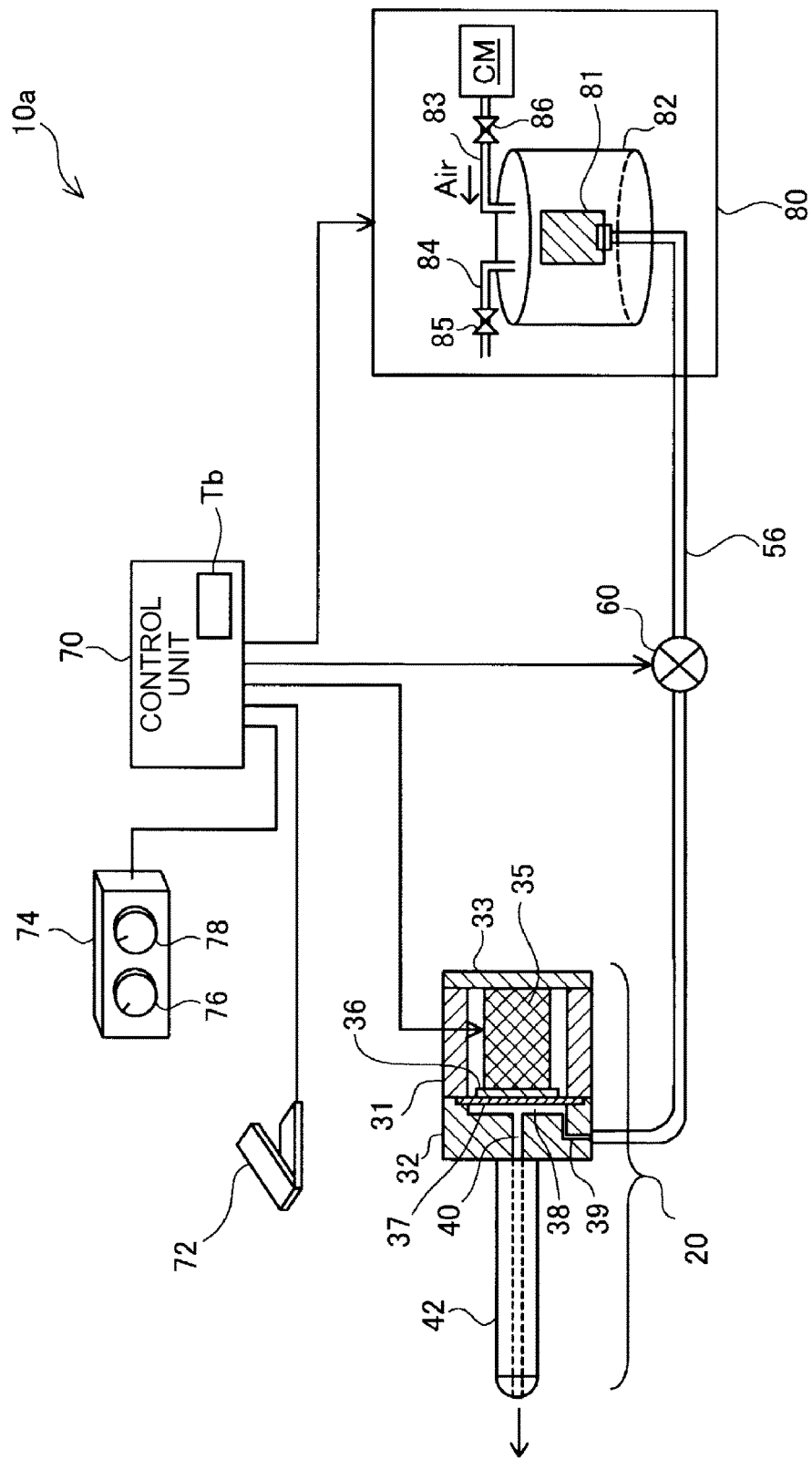

In the embodiment, the liquid supply unit 50 pressurizes the liquid with the pressurizing unit 54 using the linear motor and with the syringe 52. However, other configurations can also be employed. FIG. 9 is an explanatory view illustrating a medical apparatus system 10*a* including a liquid supply unit 80 which pressurizes a liquid with air pressure. The liquid supply unit 80 includes a film pack 81 a pressurizing chamber 82, an air supply channel 83, an air discharge channel 84, a valve 85, a valve 86, and a compressor CM. The film pack 81 accommodates a liquid. The pressurizing chamber 82 is a chamber for pressurizing the film pack 81 with the air pressure of the air supplied from the air supply channel 83. The compressor CM is connected to the air supply channel 83. In the liquid supply unit 80, the liquid in the film pack 81 can be pressurized by supplying air to the pressurizing chamber 82 by the compressor CM in the state where the valve 85 is closed. This configuration can also achieve the similar effect to the embodiment.

B2. Modification 2

Figure 10:
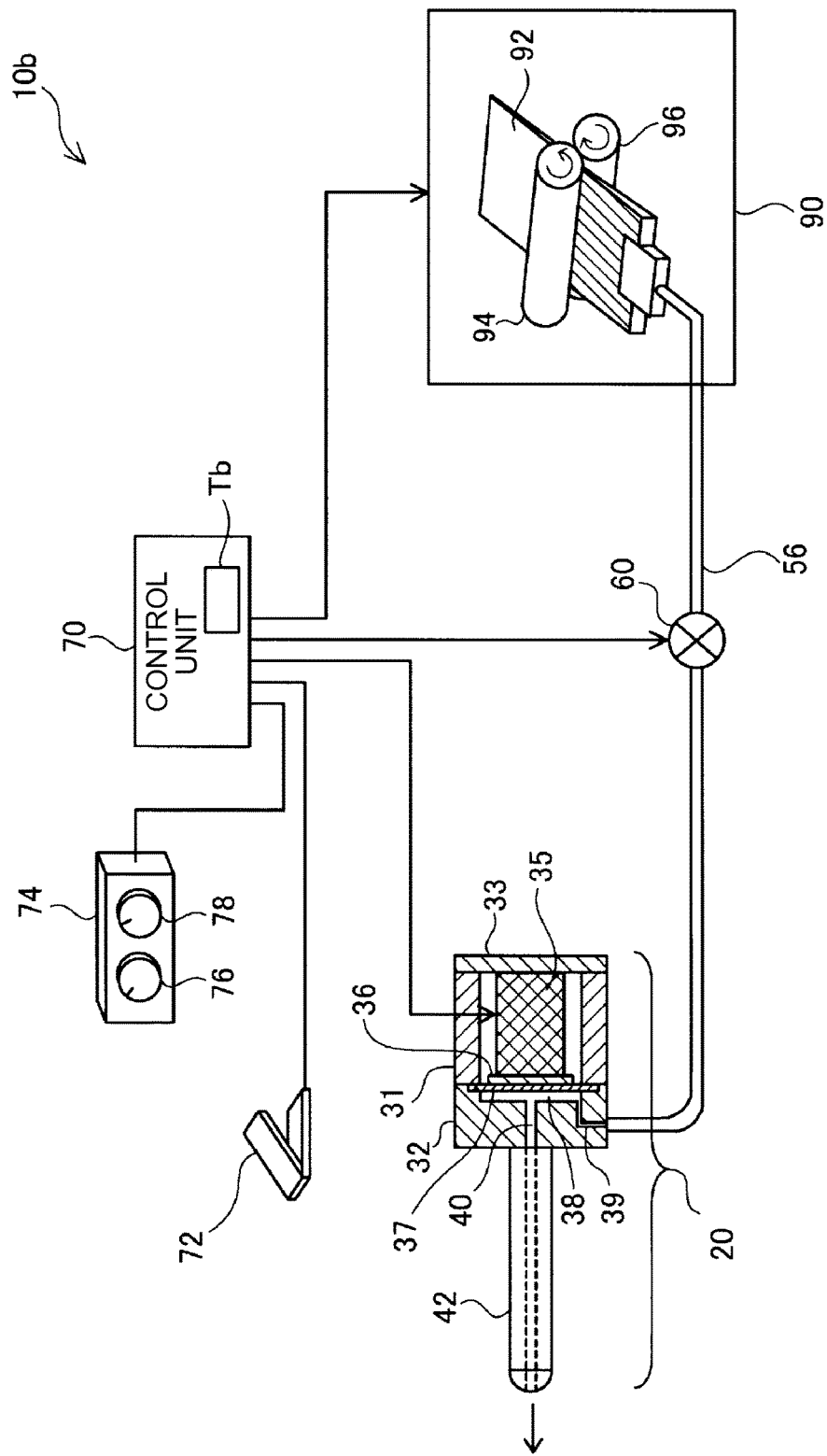
FIG. 10 is an explanatory view showing a medical apparatus system 10b.

Another configuration may be employed as the liquid supply unit. FIG. 10 is an explanatory view illustrating a medical apparatus system 10*b* including a liquid supply unit 90 which pressurizes a liquid with the rotating force of rollers. As illustrated, the liquid supply unit 90 includes a film pack 92 and rollers 94, 96. In the liquid supply unit 90, the film pack 92 is sandwiched between the rollers 94, 96 and the rollers 94, 96 are rotated, thus pressurizing the liquid in the film pack 92. The rollers 94, 96 rotate with the rotating force of a drive motor (not shown). This configuration can also achieve the similar effect to the embodiment.

B3. Modification 3

In the embodiment, the liquid ejection device 20 employs the mechanism in which the liquid inside the housing chamber 38 is provided with pulsation by the piezoelectric element 35. As Modification 3, the liquid ejection device 20 may employ a mechanism in which a laser beam is cast onto the liquid inside the housing chamber 38 to generate air bubbles, which in turn provide pulsation for the liquid. In this case, an optical fiber cable for casting a laser beam may be provided in the housing chamber 38. Also, the liquid ejection device 20 may employ a mechanism in which an electric heater heats the liquid inside the housing chamber 38 to generate air bubbles, which in turn provide pulsation for the liquid. Also, a liquid can be supplied not only to the liquid ejection device but also to various medical apparatuses, such as an ultrasonic surgical knife which ejects a liquid or a contrast medium injection device which injects a contrast medium into a body.

B4. Modification 4

In the embodiment, as the ejection control processing is started, the control unit 70 carries out pre-pressurization processing, after the liquid supply unit 50 supplies the liquid to the liquid supply channel 56 and the liquid is supplied up to the point in the liquid supply channel 56 that is blocked by the blocking unit 60. However, the pre-pressurization processing may be carried out without supplying the liquid to the liquid supply channel 56 by the liquid supply unit 50. Also, the control unit 70 may carry out the pre-pressurization processing after the liquid supply unit 50 supplies the liquid up to the liquid ejection device 20. If the pre-pressurization processing is carried out after the liquid is supplied up to the liquid ejection device 20, the liquid ejection device 20 can be used in a short time after the pre-pressurization processing.

B5. Modification 5

While the table data Tb is used in the embodiment, the table data Tb may be omitted. The pre-pressurization processing in which the liquid supply channel 56 is blocked by the blocking unit 60 may be carried out for a predetermined time.

In the embodiment, the supply pressure SP and the pre-pressure RP are described as the same value. However, it is desirable that the pre-pressure RP is ⅕ of the supply pressure SP or above and is equal to or below the supply pressure SP. Since the pre-pressure RP is equal to or below the supply pressure SP, when the liquid ejection device starts ejecting the liquid, safety is secured and the liquid can be stably supplied to the medical apparatus in a short time, due to the pre-pressure RP that is equal to or below the supply pressure SP. It is more desirable that the pre-pressure RP is ½ of the supply pressure SP or above and is below the supply pressure SP. Higher safety can be achieved and the liquid can be stably supplied to the medical apparatus in a shorter time.

What is claimed is:

1. A medical apparatus system comprising:
   a medical apparatus having an ejection unit which ejects a liquid; and
   a liquid supply device which supplies the liquid to the medical apparatus,
   wherein the liquid supply device includes:
      a supply channel through which the liquid is supplied to the ejection unit;
      a pressurizing unit which pressurizes the liquid in the supply channel to a first pressure;
      a blocking unit which blocks the supply channel; and a control unit which causes the pressurizing unit to pressurize the liquid in the supply channel in the state where the supply channel is blocked by the blocking unit, wherein the ejection unit includes an actuator which provides a pulsed flow for the ejected liquid, and an applied voltage setting unit which sets an applied voltage for driving the actuator, and wherein the control unit sets the first pressure that is a pressure with which the pressurizing unit pressurizes the liquid in the supply channel in the state where the supply channel is blocked by the blocking unit, on the basis of the applied voltage that is set.

2. The medical apparatus system according to claim 1, wherein, the control unit causes the blocking unit to block the supply channel when the ejection unit stops the ejection.

3. The medical apparatus system according to claim 1, further comprising a pressure setting unit which sets a second pressure that is a pressure with which the pressurizing unit pressurizes the liquid when the ejection unit ejects the liquid, wherein the control unit sets the first pressure that is a pressure with which the pressurizing unit pressurizes the liquid in the supply channel in the state where the supply channel is blocked by the blocking unit, on the basis of the second pressure that is set.

4. A liquid supply device which supplies a liquid to a medical apparatus having an ejection unit which ejects the liquid, the device comprising:

a supply channel through which the liquid is supplied to the medical apparatus;

a pressurizing unit which pressurizes the liquid in the supply channel to a first pressure;

a blocking unit which blocks the supply channel; and a control unit which causes the pressurizing unit to pressurize the liquid in the supply channel in the state where the supply channel is blocked by the blocking unit, wherein the ejection unit includes an actuator which provides a pulsed flow for the ejected liquid, and an applied voltage setting unit which sets an applied voltage for driving the actuator, and wherein the control unit sets the first pressure that is a pressure with which the pressurizing unit pressurizes the liquid in the supply channel in the state where the supply channel is blocked by the blocking unit, on the basis of the applied voltage that is set.

* * * * *